US008889893B2

(12) United States Patent
Strebelle et al.

(10) Patent No.: US 8,889,893 B2
(45) Date of Patent: *Nov. 18, 2014

(54) PROCESS FOR THE MANUFACTURE OF 1,2-EPOXY-3-CHLOROPROPANE

(75) Inventors: Michel Strebelle, Brussels (BE); Jean-Pierre Catinat, Waudrez (BE)

(73) Assignee: Solvay (SociétéAnonyme), Brussels (BE)

( * ) Notice: Subject to any disclaimer, the term of this patent is extended or adjusted under 35 U.S.C. 154(b) by 141 days.

This patent is subject to a terminal disclaimer.

(21) Appl. No.: 12/880,210

(22) Filed: Sep. 13, 2010

(65) Prior Publication Data

US 2010/0331557 A1 Dec. 30, 2010

Related U.S. Application Data

(63) Continuation of application No. 10/534,299, filed as application No. PCT/EP03/12519 on Nov. 10, 2003, now Pat. No. 7,834,202.

(30) Foreign Application Priority Data

Nov. 12, 2002 (FR) ..................... 02 14206

(51) Int. Cl.
C07D 301/12 (2006.01)
C07D 303/08 (2006.01)
(52) U.S. Cl.
CPC ............ *C07D 301/12* (2013.01); *C07D 303/08* (2013.01)
USPC ........................................................ 549/531
(58) Field of Classification Search
USPC ........................................................ 549/531
See application file for complete search history.

(56) References Cited

U.S. PATENT DOCUMENTS

| | | | |
|---|---|---|---|
| 2,063,891 A | 12/1936 | Dreyfus | |
| 4,655,879 A | 4/1987 | Brockmann et al. | |
| 6,063,941 A | 5/2000 | Gilbeau | |
| 6,288,248 B1 | 9/2001 | Strebelle | |
| 6,350,888 B1 | 2/2002 | Strebelle et al. | |
| 6,372,924 B2 * | 4/2002 | Thiele | 549/531 |
| 6,677,467 B2 | 1/2004 | Balthasart | |
| 7,834,202 B2 * | 11/2010 | Strebelle et al. | 549/531 |
| 2004/0068127 A1 | 4/2004 | Schoebrechts et al. | |
| 2005/0054864 A1 | 3/2005 | Strebelle et al. | |
| 2006/0041150 A1 | 2/2006 | Catinat et al. | |

FOREIGN PATENT DOCUMENTS

| | | | |
|---|---|---|---|
| BE | 422877 | 8/1937 | |
| EP | 0 568 336 | 11/1993 | |
| GB | 1046521 | 1/1964 | |
| JP | 61-236749 | 10/1986 | |
| JP | 4-327582 | * 11/1992 | ........... C07D 303/08 |
| JP | 10-218810 | 8/1998 | |
| WO | 96/03362 | 2/1996 | |
| WO | 99/24164 | 5/1999 | |
| WO | 99/28029 | 6/1999 | |

OTHER PUBLICATIONS

Document what is pH by Parish Maintenance Supply, dated 1999, p. 1.*
M.G. Clerici et al., "Synthesis of Propylene Oxide from Propylene and Hydrogen Peroxide Catalyzed by Titanium Silicalite," Journal of Catalysis, 129, 159-167 (1991).
Roger A. Sheldon, et al., "Heterogeneous Catalysts for Liquid-Phase Oxidations: Philosophers' Stones or Trojan Horses?", Acc. Chem. Res., 1998 (31), 485,493.
New Experimental Chemical Course 1, Basic Operation I, Section 4, Separation and Purification, pp. 251-252, Issued Sep. 20, 1975 (with English Translation).
Copyright Mar. 1992, Advanced Organic Chemistry, $4^{th}$ Ed., pp. 889, 908 and 937.
Yong, K.C., et al., "Refining of Crude Glycerine Recovered from Glycerol Residue by Simple Vacuum Distillation," Journal of Oil Palm Research, vol. 13, N°. 2, Dec. 2001, pp. 39-44.
F. Krausz Ann. De Chimie, 12e série, t. Nov. 4-Dec. 1949, pp. 811-831.
Glycerin : An overview, Soap and Detergent Association. Copyright 1990 by the Soap and Detergent Association, 27 pages.
Chemical and Engineering News, 1948, 26 (38), pp. 2770-2771.
Fairbourn et al., "The Partial Esterification of Polyhydric Alcohols. Part XII. The Function of Ethylene-oxide Rings," J. Chem. Soc. 1932, pp. 1965-1972, Received, Apr. 6, 1932.
Clarke et al., Organic Syntheses, Coll., vol. 1, p. 233, (1941); vol. 3, p. 47, ( 1923).
Braun, Organic Syntheses, Coll., vol. 2, p. 256, (1943); vol. 6, p. 30, (1936).
Conant et al. Organic Syntheses, Coll., vol. 1, p. 292, (1941); vol. 2, p. 29, (1922).
Bull. Soc. Chim. Fr. (1943), 10, pp. 52-58, with English Translation.
"Chemical Properties and Derivatives of Glycerol", (1965), published by Glycerine Producers' Association in New York, pp. 1-20.
G.W. Busby and D.E. Gosvenor, "The Purification of Glycerin by Ion-Exchange," The Journal of the American Oil Chemists' Society, vol. 29, N°. 8, pp. 318-320 (1952).
L.L. Lamborn, "Modern Soaps, Candles and Glycerin," D. Van NOstrand Company, London, third edition 1918, pp. 542-550, 573-574.
G. Knothe, "Historical perspectives on vegetable oil-based diesel fuels", Inform, vol. 12, Nov. 2001. pp. 1103-1107.
U. Schuchardt et al., "Transesterification of Vegetable Oils: a Review," J. Braz. Chem. Soc., vol. 9, N°. 1, 199-210, 1998.

(Continued)

*Primary Examiner* — Rosalynd Keys
(74) *Attorney, Agent, or Firm* — Oblon, Spivak, McClelland, Maier & Neustadt, L.L.P.

(57) ABSTRACT

Process for the manufacture of 1,2-epoxy-3-chloropropane by reaction between allyl chloride and hydrogen peroxide in the presence of a catalyst and in the possible presence of at least one solvent, in which the allyl chloride employed comprises less than 2000 ppm by weight of 1,5-hexadiene.

17 Claims, No Drawings

(56) References Cited

OTHER PUBLICATIONS

S. Claude, "Research of new outlets for glycerol—recent developemnts in France," Fett/Lipid 101 (1999), Nr. 3, S 101-104.

C.B. Prakash,"A critical review of Biodiesel as a Transportation Fuel in Canada," for the Transportation Systems Branch Air Pollution Prevention Directorate Enviornment Canada, Mar. 25, 1998, pp. 1-104.

H. Fukuda et al., "Biodiesel Fuel Production by transesterification of Oils", Journal of Bioscience and Bioengineering, vol. 92, No. 5, pp. 405-416 (2001).

Clerici et al.—"Epoxidation of Lower Olefins with Hydrogen Peroxide and Titanium Silicalite", Journal of Catalysis 140, pp. 71-83 (1993).

* cited by examiner

PROCESS FOR THE MANUFACTURE OF 1,2-EPOXY-3-CHLOROPROPANE

REFERENCE TO PRIOR APPLICATIONS

This application is a Continuation of U.S. application Ser. No. 10/534,299, filed May 9, 2005; which is a 371 of PCT/EP03/12519, filed Nov. 10, 2003. Priority to French patent application 02/14206, filed Nov. 12, 2002, is claimed.

The invention relates to a process for the manufacture of 1,2-epoxy-3-chloropropane by reaction between allyl chloride and hydrogen peroxide.

It is known to manufacture 1,2-epoxy-3-chloropropane (or epichlorohydrin) by epoxidation of allyl chloride by means of hydrogen peroxide in the presence of methanol as solvent and in the presence of a catalyst comprising TS-1, as disclosed in U.S. Pat. No. 6,350,888.

This known process exhibits the disadvantage that the catalyst rapidly deactivates, sometimes after a few hours of operation. This necessitates, in a continuous industrial process, frequent shutdowns in order to separate the catalyst from the epoxidation medium and to replace it by fresh catalyst or by regenerated catalyst. These operations significantly increase the cost of the process.

The present invention is targeted at overcoming this disadvantage by providing a novel process in which the deactivation is greatly reduced without, however, reducing the activity of the catalyst (or the degree of conversion of the reactants, or the rate of the epoxidation reaction) and the selectivity of the epoxidation reaction.

The invention consequently relates to a process for the manufacture of 1,2-epoxy-3-chloropropane by reaction between allyl chloride and hydrogen peroxide in the presence of a catalyst and in the possible presence of at least one solvent, in which the allyl chloride employed comprises less than 2000 ppm by weight of 1,5-hexadiene.

One of the essential characteristics of the invention lies in the purity of the allyl chloride employed in the process. This is because it has been found that the use of purified allyl chloride makes it possible to increase the duration of use of the catalyst (and thus to reduce the frequency with which the catalyst has to be removed from the epoxidation medium in order to be replaced) while retaining a high activity and a high selectivity.

The purified allyl chloride employed in the process of the invention can be obtained by any appropriate known means, for example by chlorination, as disclosed in International Application WO 96/03362. The purification can also be carried out by distillation.

The purified allyl chloride employed in the process of the invention generally comprises an amount of 1,5-hexadiene of less than or equal to 1500 ppm by weight, in particular of less than or equal to 1000 ppm by weight and preferably of less than or equal to 500 ppm by weight; values of less than or equal to 400 ppm by weight and in particular of less than or equal to 300 ppm are the most advantageous, for example values of less than 200 ppm. The amount of 1,5-hexadiene present in the purified allyl chloride is usually greater than or equal to 1 ppm by weight, most frequently greater than or equal to 10 ppm by weight.

Without being committed to a scientific theory, the Applicant Company believes that the 1,5-hexadiene is responsible at least in part for the problem of the deactivation of the catalyst. This might be explained by the fact that 1,5-hexadiene would also react with the hydrogen peroxide in the presence of the catalyst and would thus form heavy byproducts, for example products with the empirical formula $C_7H_{14}O_3$. This family of products would result from the double epoxidation and from the partial methanolysis of the 1,5-hexadiene, when methanol is used as solvent. The product concerned can, for example, be 1,2-epoxy-5-hydroxy-6-methoxyhexane. These heavy products might have the effect of blocking the pores of the catalyst and thus of reducing its activity.

The epoxidation medium in which the epoxidation reaction of the process according to the invention takes place generally comprises a liquid phase, comprising allyl chloride, hydrogen peroxide, the solvent, the 1,2-epoxy-3-chloropropane formed and optionally byproducts, and a solid phase comprising the catalyst. The liquid phase of the epoxidation medium also generally comprises water, typically in a concentration of 5 to 25% by weight. In an alternative form, the epoxidation medium can comprise 2 liquid phases, one essentially aqueous and one essentially organic.

In the process according to the invention, the hydrogen peroxide is advantageously employed in the form of an aqueous solution. The aqueous solution generally comprises at least 10% by weight of hydrogen peroxide, in particular at least 20% by weight. It usually comprises at most 70% by weight of hydrogen peroxide, in particular 50% by weight.

Generally, the molar ratio of the amount of allyl chloride employed to the amount of hydrogen peroxide employed is greater than or equal to 0.1, in particular greater than or equal to 0.5 and preferably greater than or equal to 1. This ratio is usually less than or equal to 100, more especially less than or equal to 50, generally less than or equal to 25. In a particularly advantageous alternative form of the process according to the invention, use is made of an excess of allyl chloride so that the molar ratio of the amount of allyl chloride employed to the amount of hydrogen peroxide employed is greater than or equal to 2, in particular greater than or equal to 3, very particularly greater than or equal to 4. In this advantageous alternative form, the ratio is generally less than or equal to 10, more especially less than or equal to 8 and usually less than or equal to 7. A ratio of approximately 5 is particularly well suited. The use of an excess of allyl chloride in this alternative form makes it possible to obtain an even greater increase in the selectivity (and therefore a reduction in the formation of undesirable byproducts) and, in combination with the purified allyl chloride, makes it possible to also obtain a reduction in the deactivation of the catalyst.

The solvent used in the process according to the invention can be chosen from any organic solvent which is at least partially soluble in water, and their mixtures. Solvents which are particularly suitable are alcohols. The preferred alcohols comprise from 1 to 5 carbon atoms. Those which comprise a single —OH group are highly suitable. Mention may be made, as examples, of methanol, ethanol, n-propanol, isopropanol, (tert-)butanol and pentanol. Generally, it is methanol or tert-butanol. Methanol is the commonest.

When the epoxidation medium comprises only a single liquid phase, the latter generally comprises at least 30% by weight of solvent, in particular at least 50% by weight. This amount is usually at most 90% by weight, more especially at most 75% by weight. When the epoxidation medium comprises two liquid phases, the epoxidation medium can comprise less solvent and may even be devoid of solvent.

The catalyst used in the process according to the invention generally comprises a zeolite, namely a solid comprising silica which exhibits a microporous crystalline structure. The zeolite is advantageously devoid of aluminium. It preferably comprises titanium.

The zeolite which can be used in the process according to the invention can have a crystalline structure of ZSM-5, ZSM- 11 or MCM-41 type or of zeolite beta type. Zeolites of ZSM-5 type are highly suitable. Those exhibiting an infrared absorption band at approximately 950-960 cm$^{-1}$ are preferred.

The zeolites which are particularly well suited are the titanium silicalites. Those corresponding to the formula $xTiO_2(1-x)SiO_2$ in which x is from 0.0001 to 0.5, preferably from 0.001 to 0.05, and exhibiting a crystalline structure of ZSM-5 type give particularly favourable results. Such zeolites are generally known under the name TS-1.

The catalyst is advantageously provided in the form of spherical particles obtained by any known method. A method which is particularly well suited is that disclosed in International Application WO 99/24164 from Solvay (Société Anonyme). The catalyst can also be provided in the form of non-spherical particles obtained, for example, by extrusion as disclosed in International Application WO 99/28029 from Solvay (Société Anonyme).

The catalyst particles generally exhibit a mean diameter of greater than or equal to 0.01 mm and less than or equal to 5 mm, a specific surface of greater than or equal to 1 m$^2$/g and less than or equal to 900 m$^2$/g (determined according to the nitrogen adsorption method), a bulk density of between 0.1 and 1.0 g/ml, a pore volume of between 0.15 and 2.5 ml/g and a distribution of the diameters of the pores with a maximum of between 15 and 2000 Å.

The catalyst can be present in the process according to the invention in the form of a bed. It can be a stationary bed or a fluid bed. A fluid bed is preferred.

The epoxidation reaction of the process according to the invention can be carried out in any type of appropriate reactor. It can, for example, be a single-pass bed. It can also be a reactor of loop type comprising recirculation of the epoxidation medium, with or without recirculation of the catalyst.

The temperature at which the epoxidation reaction can be carried out is generally greater than or equal to 0° C., in particular greater than or equal to 35° C., more particularly greater than or equal to 45° C. and preferably greater than or equal to 55° C. The temperature is usually less than or equal to 120° C., more especially less than or equal to 100° C., generally less than or equal to 80° C., temperatures of less than or equal to 65° C. giving highly satisfactory results. When the temperature is from 45 to 80° C., the advantage is observed, in comparison with a lower temperature, for example of approximately 35° C., that the rate of deactivation of the catalyst is also reduced.

In the process according to the invention, it may furthermore prove to be advantageous to maintain the pH of the liquid phase of the epoxidation medium during the epoxidation at a selected value. The latter corresponds, during a measurement carried out at ambient temperature with a Metrohm® 6.0239.100 electrode (electrolyte 3M KCl) on a withdrawn sample of the epoxidation medium, to values of greater than or equal to 1.5, in particular of greater than or equal to 3, more particularly of greater than or equal to 3.2. The pH is advantageously maintained at a value of less than or equal to 5, more especially of less than or equal to 4.8, values of less than or equal to 4.5 giving good results. When the pH is maintained at a value of greater than or equal to 3 and of less than or equal to 4.5, the advantage is observed, in comparison with a process carried out at natural pH without control of the pH, that the selectivity is higher without a reduction in the activity.

The pH can be controlled by addition of a base or of a mixture of a salt and of its conjugate base or acid. The base can be chosen from water-soluble bases. They can be strong bases or weak bases. Mention may be made, as examples, of an alkali metal or alkaline earth metal hydroxide, carbonate or acetate. Sodium hydroxide is preferred.

The process of the invention can be carried out at any pressure. The epoxidation medium may, if appropriate, be composed of a liquid at boiling point.

The process according to the invention can be carried out continuously or batchwise.

EXAMPLES

The tests were carried out in a plant composed essentially of a tubular reactor, jacketed under pressure, in a liquid-solid fluidized bed (diam.: 1.5 cm, h: 50 cm), with a recirculation loop. The loop comprises in particular a reflux condenser, at atmospheric pressure, positioned directly at the outlet of the reactor (condensation of the allyl chloride), and a pH probe, making it possible to regulate the pH. The overall volume of the plant was approximately 350 ml.

The temperature of the reactor was regulated using a cryothermostat.

The pressure in the reactor was regulated at 4.5 bar using a pneumatic valve.

The epoxidation medium was reduced in pressure from its exit from the reactor and the liquid-gas mixture resulting therefrom was cooled by passing into a jacketed glass coil. The set point of the cryothermostat was fixed at –20° C.

The liquid phase was divided into two streams at the outlet of the condenser:

the liquid outflow, the flow rate of which corresponded to that of the reactant feeds, and a second greater outflow, which formed the recirculation stream. The $H_2O_2$, allyl chloride (ALC) and methanol ($CH_3OH$) feeds were added to this recirculation stream. It is also at this level that the system for measuring and regulating the pH was situated.

Movement towards the reactor was provided by a membrane pump. The recirculation flow rate was measured using a flow meter and was adjusted to 5 l/h. Before entering the reactor, the liquid passed through a preheater.

Use was made, in these tests, of 18.6 g of a catalyst (i.e. 6.5 g of TS-1) provided in the form of 0.4-0.6 mm beads composed of Ti silicalite (35 weight %) dispersed in a microporous silica matrix (65 weight %). They were prepared according to a sol-gel process in the presence of a gas phase [as disclosed in WO 99/24164 from Solvay (Société Anonyme)].

The feed flow rates corresponding to the two types of epoxidation medium used are shown below.

Epoxidation Medium 1:

ALC/$H_2O_2$: 2 mol/mol $CH_3OH$/ALC: 7.8 mol/mol

ALC: 38.2 ml/h $CH_3OH$: 148.2 ml/h 39 weight % $H_2O_2$: 20.5 g/h

Epoxidation Medium 2:

ALC/$H_2O_2$: 5 mol/mol $CH_3OH$/ALC: 2.1 mol/mol

ALC: 95.5 ml/h $CH_3OH$: 99.7 ml/h 39 weight % $H_2O_2$: 20.5 g/h

The degree of conversion (DC) of the $H_2O_2$ was calculated from the inlet and outlet flow rates of the $H_2O_2$, the latter being determined using the results of the iodometric assay of the residual $H_2O_2$ in the overflow liquid, according to the following formula:

$$DC(\%)=100\times(H_2O_2 \text{ employed in mol/h} - \text{unconverted } H_2O_2 \text{ in mol/h})/H_2O_2 \text{ employed in mol/h, in which unconverted } H_2O_2 = \text{concentration of } H_2O_2 \text{ in the overflow in mol/kg} \times \text{overflow flow rate in kg/h.}$$

The term "C3 formed" is understood to denote, in the text which follows, epichlorohydrin (EPI) and the various byproducts resulting from the opening of the oxirane ring, namely 1-chloro-3-methoxy-2-propanol (recorded as 1C3OMe2Pol), 1-chloro-2-methoxy-3-propanol (recorded as 1C2OMe3Pol), 3-chloro-1,2-propanediol (MCG) and 1,3-dichloro-2-propanol (1,3DCPol).

The EPI/C3 formed selectivity can thus be calculated, from the chromatogram obtained by vapour-phase chromatography of the liquid outflow, using the expression:

$$EPI/C3f \text{ selectivity}(\%)=100\times EPI_{formed} \text{ in mol/h}/\Sigma(EPI+1C3OMe2Pol+1C2OMe3Pol+MCG+1,3DCPol)_{formed} \text{ in mol/h.}$$

Examples 1 to 7

Two grades of ALC were tested during these tests:
an ALC described as "standard", comprising 2.7 g of 1,5-hexadiene/kg
an ALC described as "high purity", comprising 180 ppm of 1,5-hexadiene.

In Examples 1 and 2, the epoxidation was carried out at a temperature of 35° C., an ALC/$H_2O_2$ molar ratio of 2 mol/mol and a $CH_3OH$/ALC molar ratio of 7.8 mol/mol. The results in terms of degree of conversion are given in Table 1.

TABLE 1

| | $H_2O_2$ Degree of conversion (%) | |
| --- | --- | --- |
| Time (h) | Example 1 "standard" ALC | Example 2 "high purity" ALC |
| 6 | 75.7 | 84.4 |
| 27 | 26.8 | 44.7 |
| 100 | | 28.3 |
| 147 | | 25.1 |

In Examples 3 and 4, the epoxidation was carried out at a temperature of 55° C., an ALC/$H_2O_2$ molar ratio of 2 mol/mol and a $CH_3OH$/ALC molar ratio of 7.8 mol/mol. The results in terms of degree of conversion are given in Table 2.

TABLE 2

| | H2O2 Degree of conversion (%) | |
| --- | --- | --- |
| Time (h) | Example 3 "standard" ALC | Example 4 "high purity" ALC |
| 6 | 89.0 | 93.9 |
| 27 | 67.5 | 79.2 |
| 120 | 33.0 | 54.2 |
| 292 | | 41.0 |

In Examples 5 to 7, the epoxidation was carried out at a temperature of 55° C., an ALC/$H_2O_2$ molar ratio of 5 mol/mol and a $CH_3OH$/ALC molar ratio of 2.1 mol/mol. In Example 7, with conditions identical to Examples 5 and 6, a "high purity" ALC was employed and, at the same time, the reactor was fed with 1,5-hexadiene so that the total flow rate of 1,5-hexadiene ("high purity" ALC+addition) is identical to that of an example with "standard" ALC. The results in terms of degree of conversion are given in Table 3.

TABLE 3

| | $H_2O_2$ Degree of conversion (%) | | |
| --- | --- | --- | --- |
| Time (h) | Example 5 "standard" ALC | Example 6 "high purity" ALC | Example 7 "high purity" ALC +1,5-hexadiene |
| 6 | 92.2 | 96.0 | 94.5 |
| 27 | 70.7 | 94.0 | 80.2 |
| 101 | 27.2 | 79.4 | |
| 120 | 25.0 | 75.0 | 37.6 |
| 194 | | 68.4 | |

A rapid deactivation is observed in Example 7, although slightly less marked than in Example 5 with a "standard" ALC. The conversion of the $H_2O_2$ after 120 h, equal to 37.6%, was markedly lower than that observed with "high purity" ALC low in 1,5-hexadiene (75%) and slightly greater than that observed with a "standard" ALC (25%). The presence of greater amounts of 1,5-hexadiene in the "standard" ALC might therefore largely explain the effect observed. The higher conversion than that observed with the "standard" ALC nevertheless indicates that other impurities (1,4-hexadiene, methylcyclopentene, and the like) might also influence the rate of deactivation.

The invention claimed is:

1. A process for manufacturing 1,2-epoxy-3-chloropropane, the process comprising reacting allyl chloride and hydrogen peroxide in the presence of a zeolite catalyst and in the optional presence of at least one solvent,
wherein:
the allyl chloride comprises less than 2000 ppm by weight of 1,5-hexadiene; and
the zeolite catalyst comprises TS-1.

2. The process according to claim 1, wherein the allyl chloride comprises less than 1500 ppm by weight of the 1,5-hexadiene.

3. The process according to claim 2, wherein the allyl chloride comprises less than 300 ppm by weight of the 1,5-hexadiene.

4. The process according to claim 1, wherein the reaction is carried out at a temperature from 45 to 80° C.

5. The process according to claim 1, wherein the reaction is carried out at a pH maintained at a value from 3 to 4.5.

6. The process according to claim 1, wherein amounts of allyl chloride and hydrogen peroxide are such that their molar ratio is from 2 to 7.

7. The process according to claim 1, comprising reacting allyl chloride and hydrogen peroxide in the presence of a zeolite catalyst and in the presence of at least one solvent comprising methanol.

8. The process according to claim 1, wherein the zeolite catalyst consists of TS-1.

9. The process according to claim 1, wherein the catalyst is present in the form of a fluid bed.

10. The process according to claim 1, wherein the reaction is carried out in a loop reactor such that the reaction medium is recirculated.

11. The process according to claim 1, comprising reacting allyl chloride and hydrogen peroxide in the presence of a zeolite catalyst and not in the presence of at least one solvent.

12. The process according to claim 1, comprising reacting allyl chloride and hydrogen peroxide in the presence of a zeolite catalyst and in the presence of at least one solvent.

13. The process according to claim 12, wherein said at least one solvent comprises at least one $C_1$-$C_5$ alcohol.

14. The process according to claim 2, wherein the allyl chloride comprises less than 1000 ppm by weight of the 1,5-hexadiene.

15. The process according to claim 2, wherein the allyl chloride comprises less than 500 ppm by weight of the 1,5-hexadiene.

16. The process according to claim 1, wherein a molar ratio of the amount of allyl chloride to the amount of hydrogen peroxide is greater than or equal to 1 and less than or equal to 25.

17. The process according to claim 1, wherein the reaction is carried out at a temperature from 45 to 80° C., the reaction is carried out at a pH maintained at a value from 3 to 4.5, and the amounts of allyl chloride and hydrogen peroxide are such that their molar ratio is from 2 to 7.

\* \* \* \* \*